United States Patent
Gingrich et al.

(10) Patent No.: US 9,964,093 B2
(45) Date of Patent: May 8, 2018

(54) TWO-DIMENSIONAL IGNITER FOR TESTING IN-CYLINDER GAS VELOCITY AND/OR GAS COMPOSITION

(71) Applicant: Southwest Research Institute, San Antonio, TX (US)

(72) Inventors: Jess W. Gingrich, San Antonio, TX (US); Manfred Amann, San Antonio, TX (US); Barrett W. Mangold, Hondo, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 107 days.

(21) Appl. No.: 14/554,515

(22) Filed: Nov. 26, 2014

(65) Prior Publication Data
US 2016/0146177 A1 May 26, 2016

(51) Int. Cl.
*F02P 17/12* (2006.01)
*G01M 15/08* (2006.01)
(Continued)

(52) U.S. Cl.
CPC ............. *F02P 17/12* (2013.01); *G01M 15/08* (2013.01); *G01N 27/226* (2013.01);
(Continued)

(58) Field of Classification Search
CPC .......... F02P 17/12; F02P 2017/121–2017/128; F02P 2017/006; G01M 15/08; H01T 1/12; G01N 2027/222
(Continued)

(56) References Cited

U.S. PATENT DOCUMENTS 4,494,508 A * 1/1985 Ma ................. F02P 5/1455
                                                    123/169 PA
4,535,738 A * 8/1985 Ma ................. F02P 5/1455
                                                    123/406.12
(Continued)

FOREIGN PATENT DOCUMENTS

GB        2286888 A * 8/1995 ........... F02D 35/021
JP     2009013850 A * 1/2009
(Continued)

OTHER PUBLICATIONS

Machine translation of WO 9114867 A1.*
(Continued)

*Primary Examiner* — Peter Macchiarolo
*Assistant Examiner* — David L Singer
(74) *Attorney, Agent, or Firm* — Livingston Law Firm

(57) ABSTRACT

An igniter system for measuring gas velocity and/or gas composition within the combustion chamber of an internal combustion engine. The igniter has an insulator body and conductive shell around the top portion of the insulator body, configured so that the igniter can be installed in place of a conventional spark plug. The igniter has two pairs of electrodes, each pair of electrodes providing a spark gap and operable to generate a spark within the combustion chamber. An activation and measurement unit is operable to generate a sustained arc in each spark gap, and to measure the voltage, current and capacitance in a measurement circuit associated with each spark gap. From various electrical measurements, the velocity and composition of the gas in the combustion chamber can be determined.

5 Claims, 4 Drawing Sheets

(51) Int. Cl.
*G01N 27/22* (2006.01)
*F02P 17/00* (2006.01)
*H01T 13/00* (2006.01)
*G01N 27/02* (2006.01)

(52) U.S. Cl.
CPC ........ *F02P 2017/006* (2013.01); *G01N 27/02* (2013.01); *G01N 2027/222* (2013.01); *H01T 13/00* (2013.01)

(58) Field of Classification Search
USPC .............................. 73/114.62–114.67, 114.08
See application file for complete search history.

(56) References Cited

U.S. PATENT DOCUMENTS

| | | | | | |
|---|---|---|---|---|---|
| 5,317,268 | A | * | 5/1994 | Maruyama | H01T 13/48 324/402 |
| 5,983,862 | A | * | 11/1999 | Nishiyama | F02P 17/12 123/406.26 |
| 6,279,538 | B1 | * | 8/2001 | Herweg | F02D 35/021 123/406.26 |
| 2002/0180326 | A1 | * | 12/2002 | Francesconi | H01T 13/54 313/140 |
| 2009/0126710 | A1 | | 5/2009 | Alger et al. | |
| 2009/0188458 | A1 | * | 7/2009 | Visser | F02D 35/021 123/169 R |
| 2010/0057327 | A1 | * | 3/2010 | Glugla | F02D 35/028 701/103 |
| 2016/0010616 | A1 | * | 1/2016 | Kimura | F02D 41/18 123/146.5 R |

FOREIGN PATENT DOCUMENTS

SU 1509745 A1 * 9/1989
WO WO 9114867 A1 * 10/1991 .............. F02P 15/02

OTHER PUBLICATIONS

Jaehong Kim, et al, "Spark Anemometry of Bulk Gas Velocity at the Plug Gap of a Firing Engine", SAE Technical Paper #952459, presented at Fuels & Lubricants Meeting & Exposition, Oct. 16-19, 1995.

* cited by examiner

TWO-DIMENSIONAL IGNITER FOR TESTING IN-CYLINDER GAS VELOCITY AND/OR GAS COMPOSITION

TECHNICAL FIELD OF THE INVENTION

This invention relates to internal combustion engines, and more particularly to instruments for testing the performance of such engines.

BACKGROUND OF THE INVENTION

As internal combustion engines are required to achieve greater efficiency, it becomes increasingly important to understand the combustion process and the state of the in-cylinder charge prior to combustion. A better understanding of the in-cylinder charge motion and its composition can be used to improve engine and combustion chamber design.

A variety of new technologies to improve engine efficiency call for new diagnostics and analysis methods, particularly of the combustion charge. For example, variable Miller cycle engines are effective at reducing pumping work and increasing expansion ratios. However, the in-cylinder change motion generated during induction decomposes into turbulence in a manner that is highly sensitive to timing of the intake valve's opening and closing.

As another example, by determining values for total inert dilution when operating engines with internal exhaust gas recirculation, through phasing of the intake and exhaust valves or when using cooled external recirculated exhaust gas or a combination of internal and external recirculated exhaust gas, useful prediction of combustion behavior can be made. However, determining total inert dilution levels in real time on a running engine can be challenging with current diagnostic and analysis methods.

As a third example, dedicated exhaust gas recirculation with in-cylinder reformation introduces high levels of untraditional compounds, specifically H2 and CO. The ability to predict the charge characteristics in real time would be beneficial for engine control and calibration purposes.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

The following description is directed to a two-dimensional igniter, which measures gas velocity in a combustion chamber of an internal combustion engine. Two pairs of parallel plates provide two spark gaps so that the flow velocity can be measured in two directions simultaneously. The igniter can also be used to derive the composition of the gas. Direct electrical measurements may be made in real time while the engine is in operation.

Figure 1:
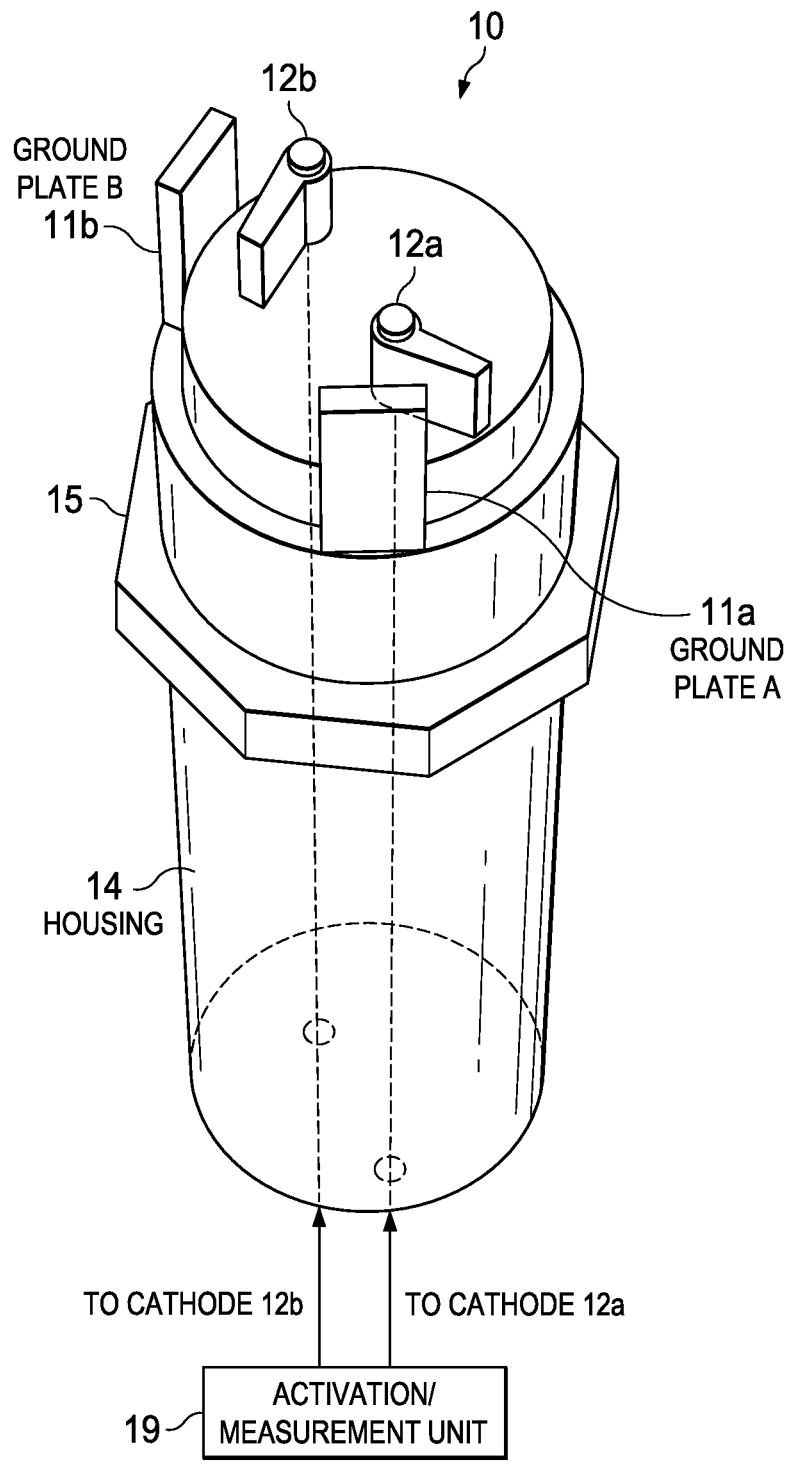
FIG. 1 is a side perspective view of the igniter.
Figure 2:
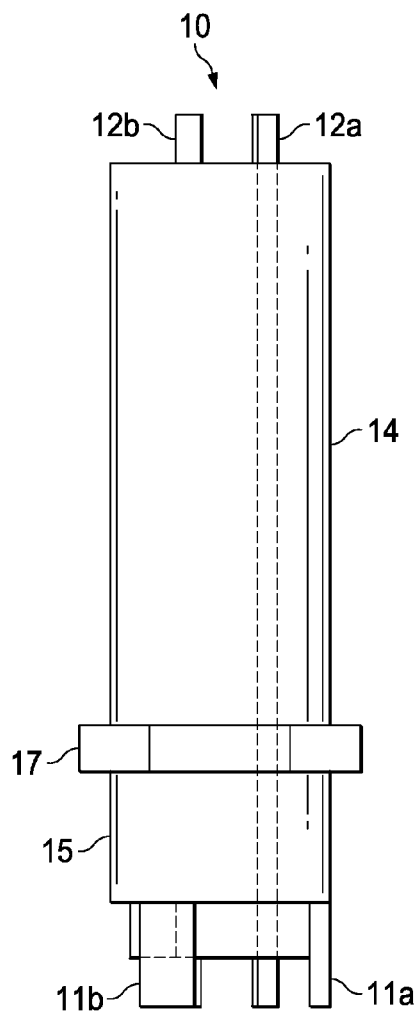
FIG. 2 is a side view of the igniter.

FIGS. 1 and 2 are a top perspective view and a side view, respectively, of a two-dimensional igniter 10. As further explained below, igniter 10 is configured so that it may be installed in an engine in place of a conventional spark plug.

As illustrated, igniter 10 has two pairs of spark gaps. Each spark gap is capable of igniting the in-cylinder charge in a manner similar to a conventional spark plug. More specifically, each spark gap of igniter 10 is operable in a manner similar to a conventional spark plug to deliver electric current to the combustion chamber of a spark-ignition engine to ignite the compressed fuel/air mixture by an electric spark.

In the example of this description, the spark gaps are between two pairs of parallel plates. For each spark gap, one plate provides an anode 11a or 11b and the other a cathode 12a or 12b. Electrode geometries other than parallel plates are possible.

A feature of the invention is that the two pairs of electrodes are positioned so that their spark gaps are angled relative to each other. In other words, the electrical arcs generated between the spark gaps are angled relative to each other. In the example of this description, the two spark gaps are orthogonal, that is, they produce electrical arcs that are at a ninety degree angle. However, other angular relationships between the two spark gaps (and hence their arcs) are possible. In general, the angular relationship between the two spark gaps can be between 0 and 180 degrees.

The cathode of each spark gap is connected to an activation/measurement unit 19. Activation/measurement unit 19 has a power source to provide AC, DC, or both types of current to each spark gap. Unit 19 also has a separate voltage, current and capacitance measurement circuit for each spark gap. An example of a suitable such circuit is described below in connection with FIG. 5.

The power source of unit 19 is operable to provide a spark gap breakdown voltage, as well as a controlled arc event between each of the spark gaps. The two spark gaps may be energized independently or simultaneously. As explained below, the power source is capable of providing an arc event of duration longer than that of a conventional spark plug discharge.

Igniter 10 has an outer shell 15, electrically isolated from the central electrodes (cathodes 12a and 12b) by a cylindrical insulator body 14. Shell 15 is made from a conductive material, such as metal, and circumferentially surrounds a top portion (near the face end) of igniter 10. The shell 15 has threads and a flanged head 17 that allow it to be installed into a conventional spark plug bore of an engine cylinder head.

Each of the two central electrodes (cathodes) 12a and 12b, which may contain a resistor, is connected by an insulated wire to an output terminal of activation/measurement unit 19. The metal shell 15 is screwed or otherwise installed into the engine's cylinder head, and its outer electrodes (anodes) are thereby electrically grounded.

Each central electrode 12a and 12b protrudes through the insulator 14 at the face of the igniter, into the combustion chamber. For each pair of electrodes, a spark gap is formed between the central electrode and the ground electrode.

Figure 3:
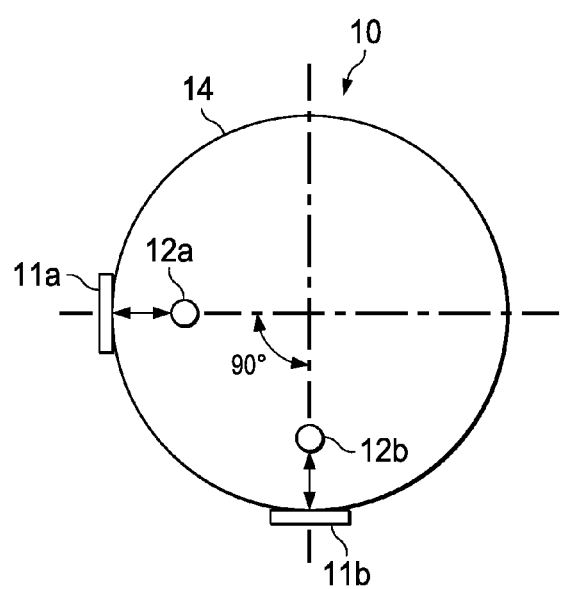
FIG. 3 is a top view of the face of the igniter.

FIG. 3 is a top plan view of the face plane of the igniter 10. The two spark gaps are indicated by arrows. Referring again to FIG. 1, as indicated by the dotted lines, each spark gap has a corresponding measurement "axis" connected to its associated measurement circuit of activation/measurement unit 19.

Referring to FIGS. 1-3, a first spark gap is between ground plate 11a and cathode 12a. A second spark gap is between ground plate 11b and cathode 12b.

The spark gaps between the electrodes are angled relative to each other on the face plane of the igniter 10. The angle between the spark gaps is illustrated by the dotted lines A and B of FIG. 3, which are at a 90 degree (orthogonal) angle.

In addition to being orthogonal, the two spark gaps are in the same plane relative to the face of the igniter. In other words, the two electrical arcs between the pair of spark gaps are in the same plane.

Using activation/measurement unit 19, each spark gap can be independently activated to ignite the charge, or to provide a measurement signal, or both. In other words, one of the spark gaps can be used as a spark plug igniter to initiate combustion while the other spark gap is used to carry out charge flow and charge gas composition measurements. If desired, these assignments can be alternated from one engine cycle to the next to quickly capture flow velocities and charge mass compositions in two directions while operating the engine at steady state.

In operation, igniter 10 is installed in an engine cylinder in place of a normal spark plug. When so installed, igniter 10 can have two measurement capabilities.

A first measurement capability of igniter 10 is to sustain an electrical arc between each of the spark gaps for gas velocity measurement data. The current and voltage needed to sustain the arc can be measured by activation/measurement unit 19. The resulting measurement indicates the velocity of the gas between the electrodes. A pair of measurements provides gas velocity in two dimensions.

A second measurement capability of igniter 10 is to measure capacitance between each spark gap for gas composition measurement data. The capacitance measurement indicates the composition of the gas between the electrodes, once other factors are calibrated for.

More specifically, with regard to measuring gas velocity, activation/measurement unit 19 is used to create the voltage necessary to generate an arc between the electrodes. The electrical source then provides continuous energy to sustain the arc over a longer period of time. For purposes of this description, a "sustained" arc is one longer than that required for ignition in conventional engine operation. An example of a suitable time for measurement is approximately 1-10 ms. The "holding current" to sustain the arc may be lower than that required to generate the arc.

Appropriate instruments (voltmeter and ammeter) are included in activation/measurement unit 19 to measure voltage and current in each measurement axis. It has been demonstrated by previous research that an approximate value of the bulk flow velocity of a gas through an arc between a spark gap may be deduced from the voltage and current waveforms of the spark. This technique has become known as "spark anemometry".

Thus, for igniter 10, the resulting profile of voltage and current to sustain an arc can be correlated to the gas velocity between the spark gap of either or both measurement axes. Quantifying the gas velocity in two directions, perpendicular to each other, allows for measurement of in-cylinder gas velocities at the spark plug as well as the direction of the gas flow.

Igniter 10 can be discharged throughout the compression stroke of a non-fueled (non-combustion) cycle to document in-cylinder gas velocity profiles temporally. The dual spark gap design can be further manipulated to provide feedback for different length scales that best describe turbulence.

Thus, in general, igniter 10 can be used to measure how velocity changes at the spark plug location of an engine, as a function of time or crank angle for a given combustion chamber and cam phasing. Measuring the properties of the two spark gap circuits, such as changes in voltage, current, resistance or impedance during the long arc event of a combustion or non-combustion cycle can be performed to determine the gas velocities in two dimensions.

Because igniter 10 is equivalent to a functioning spark plug, it can be operated at a steady state engine operating conditions. In this case, all the cylinder boundary conditions (pressure, temperature, and gas composition) are "real". Then, a diagnostic can be performed on one or more cycles where the cylinder is not fueled. In this "in-situ" scenario, the igniter 10 can be used for a secondary purpose, such as measuring gas velocity or composition.

With regard to using igniter 10 to measure capacitance, the two parallel plates of each spark gap act as a capacitor and can be subjected to a DC or AC potential. The response of this static or alternating potential is a function of the density of the gas between the plates. Thus, the capacitance is one property that can be measured to identify the properties of the gas between the plates.

More specifically, capacitance is a function of the area of the plates, the distance between the plates and the relative permittivity of the dielectric. For igniter 10, the area of the plates that form the spark gaps is fixed and known. If the capacitive response of a spark gap is calibrated to the nominal pressure and temperature changes during compression, then the third factor, the dielectric of the gas (directly related to composition), can be determined.

Permittivity of the in-cylinder gas mixture is sensitive to the dielectric properties of the individual components in the gas. Calibrating and amplifying the capacitance measurement for density leaves the permittivity of the gas to change with composition. Activation/measurement unit 19 may have stored data for calibration purposes, as well as for mapping permittivity to gas composition.

Figure 4:
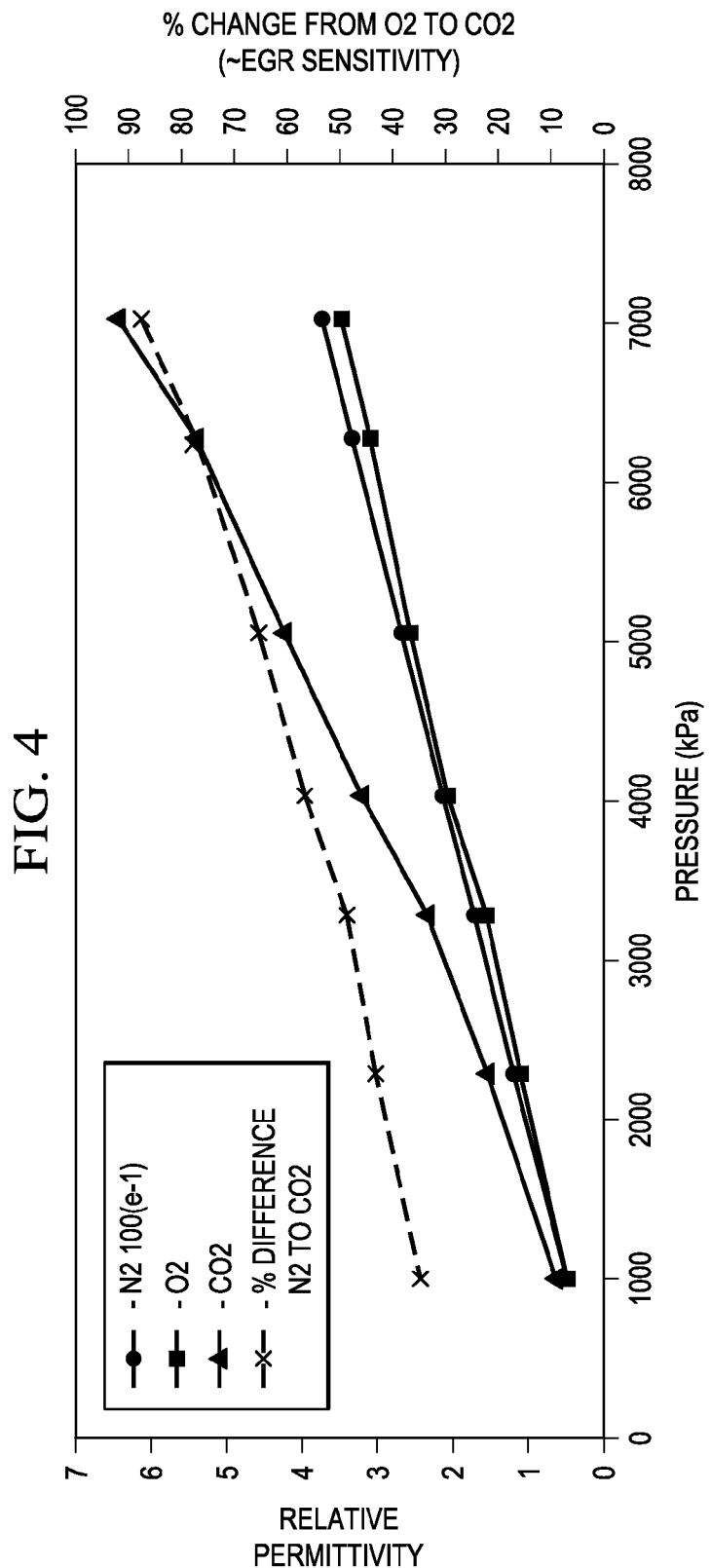
FIG. 4 illustrates the relationship between permittivity of various gases as a function of pressure, as derived from capacitance measurements.

FIG. 4 illustrates the permittivity of nitrogen (N2), oxygen (O2), and carbon dioxide (CO2) as a function of pressure. Recirculated exhaust (EGR) primarily consists of inert species such as CO2 and H2O. When EGR is mixed with fresh inlet air, the overall concentration of in-cylinder O2 decreases. The variation of in-cylinder gas composition with varying capacitance can indicate the ratio of CO2 and O2, which is directly related to the levels of exhaust dilution. This is because the permittivity of O2 and CO2 are greatly different. Thus, the capacitance of either or both spark gap measurement circuits can be used to determine the amount of exhaust gas mixed with the inducted charge.

By calibrating the capacitance measurements for a fixed amount of recirculated gas and using the permittivity difference between CO2, H2O, CO and H2, the amount of reformate present in combustion chamber before main charge ignition can be determined. The results of testing for reformate can then be used to control spark timing, or other engine variables.

The capacitance-measuring functionality of igniter 10 allows for in-cylinder measurement of total inert dilution of the charge regardless of the dilution source. The dilution source may be ambient air, from an EGR loop, or from trapped cylinder exhaust gas. Capacitance measurements can also be used to track dynamic changes in cylinder scavenging that can cause abnormal combustion at certain operating conditions.

A capacitance measurement method can be calibrated for both density and a near constant level of dilution. In a method especially useful for dedicated EGR engines, when the engine is run rich, the EGR composition change and resulting permittivity change can be measured to estimate the amount of reformate in the cylinder prior to ignition.

The above-described capacitance and permittivity measurements can be used for real time engine control. As stated above, the amount of total inert dilution, or reformate produced in a dedicated EGR engine, can be measured before ignition. In addition, real-time feedback data can be acquired about in-cylinder charge motion at the spark plug location and charge mass composition for engine control or for engine calibration. Control of the combustion process through spark timing and many other engine control-related variables can be improved. In a multi-cylinder engine, the measurements can be used to determine cylinder-to-cylinder variations and/or cycle-by-cycle variations in in-cylinder charge motion and charge mass composition, and thereby to aid design of combustion chamber components and intake and exhaust systems.

Figure 5:
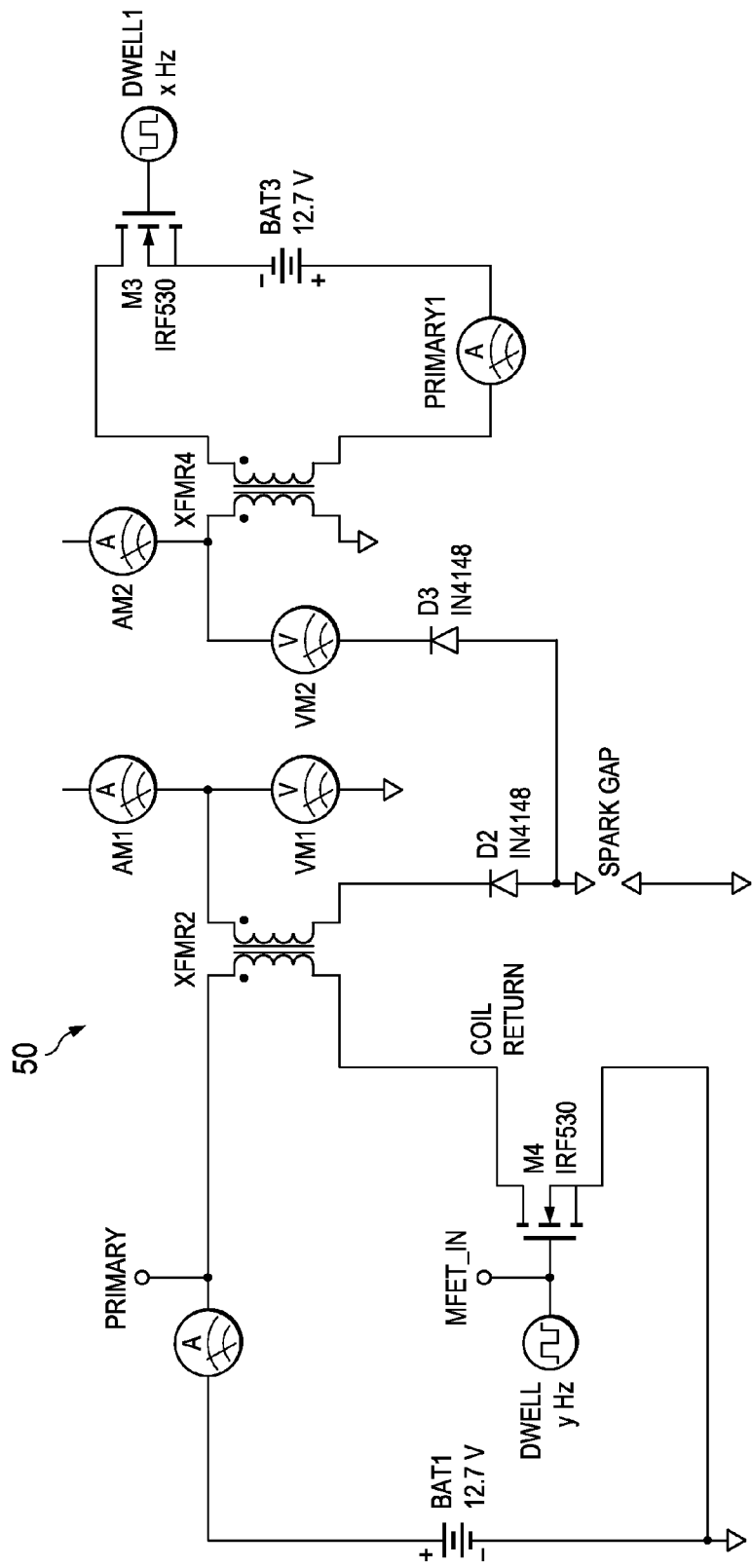
FIG. 5 is an example of an activation/measurement circuit, which is part of the activation/measurement unit of FIG. 1.

FIG. 5 illustrates an example of a portion of the activation/measurement unit 19 of FIG. 1. One activation/measurement circuit 50 for one spark gap is shown. Each spark gap has its own associated circuit, capable of measuring at least voltage, current and capacitance between the spark gap. Each circuit has two coils to provide the extended spark duration.

As stated above, the spark duration can be controlled for typically 1 to 10 milliseconds. This extended spark duration expands the measurement range of the igniter system.

The activation/measurement unit 19 may also include processing hardware and software for performing the measurements and deriving gas velocity and gas composition as described above.

What is claimed is:

1. A method of measuring exhaust gas dilution of the in-cylinder charge within the combustion chamber of a spark ignition engine, comprising:
    installing an igniter in place of a spark plug, the igniter comprising: a cylindrical insulator body; a conductive shell around the circumference of a top portion of the insulator body; two pairs of electrodes, each pair of electrodes providing a spark gap at the face of the igniter, and each pair of electrodes having an cathode electrode and a ground electrode; wherein the pairs of electrodes are positioned such that the spark gaps are angled relative to each other and in the same plane relative to and extending from the face of the igniter; an activation and measurement unit in electrical connection with each pair of electrodes and operable to: activate the cathode electrodes to generate a spark in each spark gap, to provide sufficient current to the cathode electrodes to generate a sustained arc in each spark gap, to measure the voltage and current in each measurement circuit;
    activating both pairs of electrodes during an engine combustion cycle;
    wherein one pair of electrodes is activated solely to initiate combustion and the other pair of electrodes is activated solely to measure capacitance between the electrodes;
    measuring the capacitance, thereby obtaining a measured capacitance value;
    accessing stored data representing relationships between measured capacitance values and the ratios of carbon dioxide to oxygen in the in-cylinder charge to determine a current ratio of carbon dioxide to oxygen in the in-cylinder charge; and
    based on the current ratio of carbon dioxide to oxygen in the in-cylinder charge, estimating the amount of exhaust gas dilution in the in-cylinder charge.

2. The method of claim 1, further comprising storing calibration data to calibrate measured capacitance for gas density, thereby obtaining permittivity data, and mapping permittivity data to gas composition.

3. The method of claim 1, wherein the activating step is performed within a combustion chamber that produces dedicated exhaust gas for recirculation.

4. The method of claim 1, wherein the spark gaps are at a ninety degree angle.

5. The method of claim 1, further comprising alternating which pair of electrodes is used for ignition and which is used for measurement from one engine cycle to the next.

* * * * *